United States Patent [19]

Seufert et al.

[11] Patent Number: 4,462,997
[45] Date of Patent: Jul. 31, 1984

[54] 3-FLUOROPHENYL (DI)THIOPHOSPHATES, AND THEIR USE FOR CONTROLLING PESTS

[75] Inventors: Walter Seufert; Hans-Peter Loeffler, both of Ludwigshafen; Heinrich Adolphi, Limburgerhof, all of Fed. Rep. of Germany

[73] Assignee: BASF Aktiengesellschaft, Fed. Rep. of Germany

[21] Appl. No.: 410,878

[22] Filed: Aug. 24, 1982

[30] Foreign Application Priority Data

Aug. 28, 1981 [DE] Fed. Rep. of Germany ....... 3134136

[51] Int. Cl.³ ...................... A01N 57/14; C07F 9/165
[52] U.S. Cl. .................... 424/217; 424/224; 260/950; 260/940; 260/954; 260/951; 260/949; 260/964; 260/948
[58] Field of Search ................ 260/964, 950; 424/224, 424/217

[56] References Cited

U.S. PATENT DOCUMENTS 3,663,665 5/1972 Kume et al. ................ 260/964
3,794,734 2/1974 Cragoe, Jr. et al. ................ 424/330
3,839,511 10/1974 Kishino et al. ................ 260/964

FOREIGN PATENT DOCUMENTS 22954 1/1981 European Pat. Off. ............ 260/964
3134136 3/1983 Fed. Rep. of Germany .
2234261 1/1975 France .

Primary Examiner—Anton H. Sutto
Attorney, Agent, or Firm—Keil & Weinkauf

[57] ABSTRACT

3-Fluorophenyl (di)thiophosphates of the formula

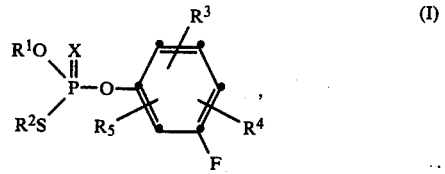

where $R^1$ is alkyl of 1 to 3 carbon atoms, $R^2$ is alkyl or haloalkyl of 1 to 5 carbon atoms, alkoxyalkyl or alkylthioalkyl of 2 to 8 carbon atoms or cycloalkyl of 3 to 6 carbon atoms, $R^3$, $R^4$ and $R^5$ independently of one another are each hydrogen, halogen, cyano, nitro, alkyl, alkoxy or alkylthio of 1 to 6 carbon atoms and X is oxygen or sulfur, a process for their preparation, and their use for controlling pests.

5 Claims, No Drawings

3-FLUOROPHENYL (DI)THIOPHOSPHATES, AND THEIR USE FOR CONTROLLING PESTS

The present invention relates to 3-fluorophenyl (di)-thiophosphates, a process for their preparation, and pesticides which contain these compounds as active ingredients.

O,S-dialkyl O-halophenyl thiophosphates which are useful for controlling pests, such as insects, arachnids and nematodes, have been disclosed in German Published Application DAS No. 2,163,391 and U.S.S.R. Pat. No. 482,460.

We have found that 3-fluorophenyl (di)thiophosphates of the formula

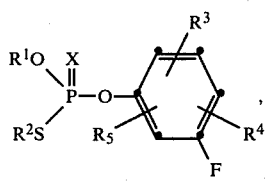
(I)

where $R^1$ is alkyl of 1 to 3 carbon atoms, $R^2$ is alkyl or haloalkyl of 1 to 5 carbon atoms, alkoxyalkyl or alkylthioalkyl of 2 to 8 carbon atoms or cycloalkyl of 3 to 6 carbon atoms, $R^3$, $R^4$ and $R^5$ independently of one another are each hydrogen, halogen, cyano, nitro, alkyl, alkoxy or alkylthio of 1 to 6 carbon atoms and X is oxygen or sulfur, are effective in controlling pests from the class comprising insects, arachnids and nematodes, and have a superior action compared with the conventional O,S-dialkyl O-halophenyl thiophosphates of similar structure.

In formula I, $R^1$ is alkyl of 1 to 3 carbon atoms, eg. methyl, ethyl, n-propyl or i-propyl, $R^2$ is alkyl or haloalkyl, each of 1 to 5 carbon atoms, eg. ethyl, n-propyl, i-propyl, n-butyl, sec-butyl, i-butyl, n-pentyl, 1-methyl-n-butyl, 3-methyl-n-pentyl, 2-choroethyl or 3-chloro-n-propyl, alkoxyalkyl or alkylthioalkyl, each of 2 to 8, preferably 2 to 5, carbon atoms, eg. 2-methoxyethyl, 2-ethoxyethyl, 2-isopropoxyethyl, 2-methylthioethyl or 2-ethylthioethyl, or cycloalkyl of 3 to 6 carbon atoms, eg. cyclopentyl or cyclohexyl, and $R^3$, $R^4$ and $R^5$ may be identical or different and are each hydrogen, halogen, eg. chlorine, bromine or fluorine, nitro or cyano, or alkyl, alkoxy or alkylthio of 1 to 4, preferably 1 or 2, carbon atoms, eg. methyl, ethyl, methoxy, ethoxy, methylmercapto or ethylmercapto.

The 3-fluorophenyl (di)thiophosphates of the formula I are obtained by reacting an O,S-dialkylphosphoric acid ester chloride of the formula

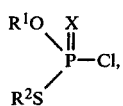
(II)

where $R^1$, $R^2$ and X have the above meanings, with a 3-fluorophenol of the formula

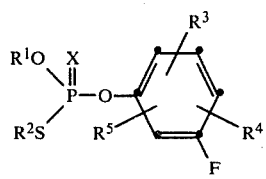
(III)

where $R^3$, $R^4$ and $R^5$ have the above meanings, in the presence or absence of an acid acceptor and in the presence of a diluent, or with a salt of a 3-fluorophenol of the formula III, in the presence or absence of a diluent.

The course of the reaction may be represented by the following equation:

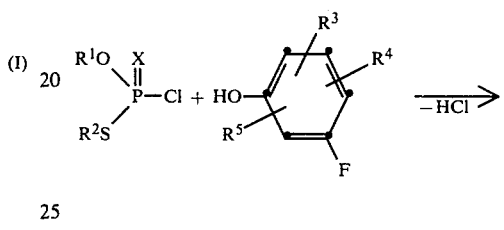

The reaction of a phosphoric acid ester chloride of the formula II with a phenol of the formula III may be carried out in an organic diluent, eg. acetone, acetonitrile, benzene, toluene, chlorobenzene or methyl ethyl ketone, or in a two-phase system, eg. toluene/water or dichloromethane/water.

Advantageously, from 1 to 2 moles of an acid acceptor are employed per mole of the phenol of the formula III, an excess of about 10% preferably being used. Bases such as alkali metal carbonates, eg. potassium carbonate, alkali metal hydroxide, eg. sodium hydroxide, and tertiary amines, eg. triethylamine, are suitable. Instead of the base and the phenol, it is also possible to react a salt of the phenol with the phosphoric acid ester chloride. Suitable salts are alkali metal, alkaline earth metal and unsubstituted or substituted ammonium salts, such as alkylammonium, eg. dimethylammonium and triethylammonium, salts, and sodium salts and calcium salts.

The reaction temperature may be varied within a relatively wide range, and is in general from room temperature to 100° C., preferably from 30° to 70° C. The reaction is carried out in general under atmospheric pressure.

In carrying out the process, the starting materials are employed in equimolar amounts, but an excess of one or other of the reactants may be advantageous in some cases. Preferably, from 0.9 to 1.1 moles of phosphoric acid ester chloride are used per mole of phenol.

The reaction mixture is worked up in a conventional manner, for example by adding water and separating the phases. The crude products can be purified by distillation or column chromatography.

O,S-Dialkylphosphoric acid ester chlorides of the formula II are known, and may be prepared by conventional processes (German Laid-Open Application DOS No. 2,642,982 and J. Org. Chem. 30, (1965), 3,217).

The 3-fluorophenols of the formula III may likewise be prepared by conventional processes (U.S. Pat. No. 3,794,734 and French Pat. No. 2,234,261).

The novel compounds may also be obtained by the following, further processes:

3-fluorophenyl thiophosphates of the formula Ia may be prepared by an Arbusow reaction, by reacting a phosphite of the formula IV with a sulfenyl chloride of the formula R²SCL, according to the following equation:

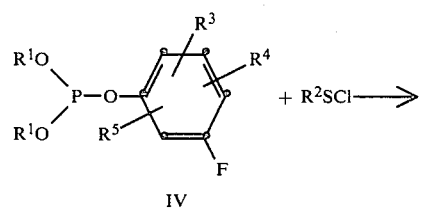

IV

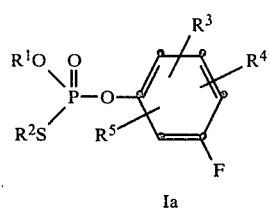

Ia

The 3-fluorophenyl thiophosphates of the formula Ia may also be obtained by alkylating a phosphoric acid ester salt of the formula V with an alkylating agent of the formula R²Y:

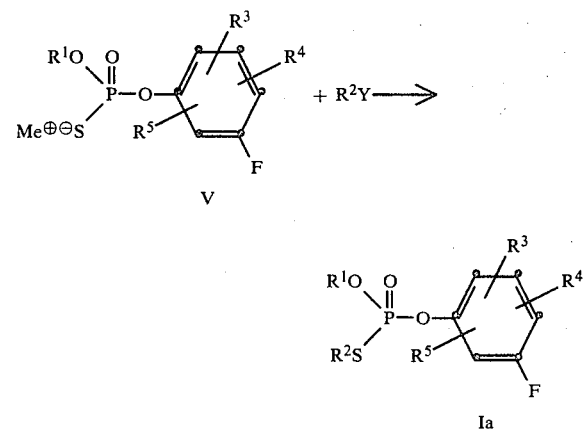

V

Ia

Furthermore, a phosphoric acid ester dichloride of the formula VI may be reacted with an alcohol of the formula R¹OH and a mercaptan of the formula R²SH to give a compound of the formula I:

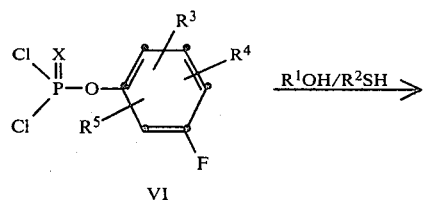

VI

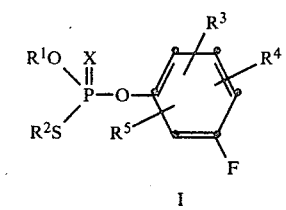

I

In these equations, $R^1$, $R^2$, $R^3$, $R^4$, $R^5$ and X have the above meanings, $Me^\oplus$ is a metal cation or an unsubstituted or alkyl-substituted ammonium ion, and Y is halogen, eg. iodine, bromine or chlorine, or alkyl-sulfate, eg. methyl-sulfate.

PREPARATION EXAMPLE 7.6 parts of potassium carbonate are added to 6.1 parts of 3-fluorophenol in 90 parts of acetonitrile, and the mixture is refluxed for one hour, while stirring. Thereafter, 10.1 parts of O-ethyl-S-propyl-thiophosphoric acid ester chloride are added dropwise at 50° C., and the mixture is stirred for 4 hours at 50° C. and then for 24 hours at room temperature. The solvent is removed in a rotary evaporator, 400 parts of toluene and 100 parts of water are added, the phases are separated, the organic phase is washed with 2N sodium hydroxide solution and then with water, and dried over sodium sulfate, and the solvent and volatile impurities are removed at 40° C., under a reduced pressure of 0.13 mbar. 10.5 g of a product of refractive index $n_D^{21} = 1.5000$ are obtained as the residue.

The following compounds may be prepared by one of the above processes:

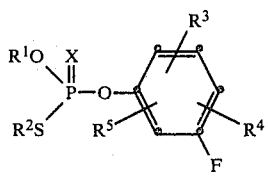

| No. | $R^1$ | $R^2$ | X | $R^3$ | $R^4$ | $R^5$ | $n_D$ |
|---|---|---|---|---|---|---|---|
| 1 | $C_2H_5$ | $n$-$C_3H_7$ | O | H | H | H | $n_D^{25} = 1.5000$ |
| 2 | $C_2H_5$ | sec.-$C_4H_9$ | O | H | H | H | $n_D^{20} = 1.5029$ |
| 3 | $C_2H_5$ | $C_2H_5$—O—$(CH_2)_2$— | O | H | H | H | $n_D^{20} = 1.5390$ |
| 4 | $C_2H_5$ | $n$-$C_3H_7$ | S | H | H | H | $n_D^{23} = 1.4990$ |

-continued

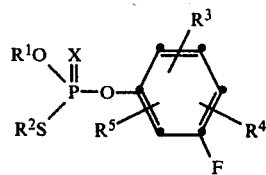

| No. | R¹ | R² | X | R³ | R⁴ | R⁵ | $n_D$ |
|---|---|---|---|---|---|---|---|
| 5 | Mixture of | | | | | | |
| | C₂H₅ | n-C₃H₇ | O | 6-Br | H | H and | |
| | C₂H₅ | n-C₃H₇ | O | H | 4-Br | H | $n_D^{22} = 1.5232$ |
| 6 | Mixture of | | | | | | |
| | C₂H₅ | sec.-C₄H₉ | O | 6-Br | H | H and | |
| | C₂H₅ | sec.-C₄H₉ | O | H | 4-Br | H | $n_D^{22} = 1.5239$ |
| 7 | Mixture of | | | | | | |
| | C₂H₅ | i-C₄H₉ | O | 6-Br | H | H and | |
| | C₂H₅ | i-C₄H₉ | O | H | 4-Br | H | $n_D^{22} = 1.5208$ |
| 8 | Mixture of | | | | | | |
| | C₂H₅ | CH₃O—(CH₂)₂— | O | 6-Br | H | H and | |
| | C₂H₅ | CH₃O—(CH₂)₂— | O | H | 4-Br | H | $n_D^{25} = 1.5210$ |
| 9 | Mixture of | | | | | | |
| | C₂H₅ | C₂H₅—O—(CH₂)₂— | O | 6-Br | H | H and | |
| | C₂H₅ | C₂H₅—O—(CH₂)₂— | O | H | 4-Br | H | $n_D^{24} = 1.5196$ |
| 10 | Mixture of | | | | | | |
| | C₂H₅ | n-C₃H₇ | S | 6-Br | H | H and | |
| | C₂H₅ | n-C₃H₇ | S | H | 4-Br | H | $n_D^{24} = 1.5595$ |
| 11 | C₂H₅ | ClCH₂—(CH₂)₂— | O | H | 4-Br | H | |
| 12 | C₂H₅ | ClCH₂—(CH₂)₂— | O | H | 4-CN | H | |
| 13 | C₂H₅ | n-C₃H₇ | O | 6-Br | 4-Br | H | $n_D^{23} = 1.5480$ |
| 14 | C₂H₅ | sec.-C₄H₉ | O | 6-Br | 4-Br | H | $n_D^{22} = 1.5437$ |
| 15 | C₂H₅ | i-C₄H₉ | O | 6-Br | 4-Br | H | $n_D^{26} = 1.5418$ |
| 16 | C₂H₅ | C₂H₅O(CH₂)₂— | O | 6-Br | 4-Br | H | $n_D^{25} = 1.5405$ |
| 17 | C₂H₅ | n-C₃H₇ | S | 6-Br | 4-Br | H | $n_D^{21} = 1.5841$ |
| 18 | C₂H₅ | sec.-C₄H₉ | S | 6-Br | 4-Br | H | $n_D^{27} = 1.5755$ |
| 19 | C₂H₅ | n-C₃H₇ | O | 6-Cl | H | H | $n_D^{25} = 1.5112$ |
| 20 | C₂H₅ | sec.-C₄H₉ | O | 6-Cl | H | H | $n_D^{22} = 1.5111$ |
| 21 | C₂H₅ | i-C₄H₉ | O | 6-Cl | H | H | $n_D^{25} = 1.5077$ |
| 22 | C₂H₅ | CH₃O(CH₂)— | O | 6-Cl | H | H | $n_D^{22} = 1.5118$ |
| 23 | C₂H₅ | C₂H₅O(CH₂)₂— | O | H | H | 6-Cl | $n_D^{22} = 1.5080$ |
| 24 | C₂H₅ | n-C₃H₇ | O | H | 4-Cl | 6-Cl | $n_D^{22} = 1.5240$ |
| 25 | C₂H₅ | sec.-C₄H₉ | O | H | 4-Cl | 6-Cl | $n_D^{22} = 1.5195$ |
| 26 | C₂H₅ | i-C₄H₉ | O | 6-Cl | 4-Cl | H | $n_D^{22} = 1.5188$ |
| 27 | C₂H₅ | CH₃O(CH₂)₂— | O | 6-Cl | 4-Cl | H | $n_D^{20} = 1.5235$ |
| 28 | C₂H₅ | C₂H₅O(CH₂)₂— | O | 6-Cl | 4-Cl | H | $n_D^{23} = 1.5145$ |
| 29 | C₂H₅ | n-C₃H₇ | S | H | 4-Cl | 6-Cl | $n_D^{22} = 1.5559$ |
| 30 | C₂H₅ | n-C₃H₇ | O | H | 4-Cl | H | $n_D^{22} = 1.5148$ |
| 31 | C₂H₅ | sec.-C₄H₉ | O | H | 4-Cl | H | $n_D^{22} = 1.5095$ |
| 32 | C₂H₅ | i-C₄H₉ | O | H | 4-Cl | H | $n_D^{22} = 1.5100$ |
| 33 | CH₃ | n-C₃H₇ | S | H | H | H | |
| 34 | CH₃ | n-C₃H₇ | O | H | H | H | |
| 35 | CH₃ | sec.-C₄H₉ | S | H | H | H | |
| 36 | CH₃ | sec.-C₄H₉ | O | H | H | H | |
| 37 | CH₃ | n-C₃H₇ | O | H | 4-Br | H | |
| 38 | CH₃ | n-C₃H₇ | O | H | 4-Cl | H | |
| 39 | CH₃ | sec.-C₄H₉ | O | H | H | 6-Cl | |
| 40 | CH₃ | n-C₃H₇ | O | H | H | H | |
| 41 | C₂H₅ | CH₃ | O | H | H | H | |
| 42 | C₂H₅ | CH₃ | O | H | 4-Cl | H | |
| 43 | C₂H₅ | CH₃ | O | H | 4-Br | H | |
| 44 | C₂H₅ | CH₃ | O | 6-Cl | H | H | |
| 45 | C₂H₅ | CH₃ | O | 6-Cl | 4-Cl | H | |
| 46 | C₂H₅ | n-C₃H₇ | O | H | 4-F | H | |
| 47 | C₂H₅ | n-C₃H₇ | O | H | 4-CN | H | |
| 48 | C₂H₅ | n-C₃H₇ | S | H | 4-Cl | H | |
| 49 | C₂H₅ | n-C₃H₇ | S | H | 4-F | H | |
| 50 | C₂H₅ | n-C₃H₇ | S | 6-Cl | H | H | |
| 51 | C₂H₅ | n-C₃H₇ | S | H | 4-CN | H | |
| 52 | C₂H₅ | i-C₃H₇ | O | H | H | H | |
| 53 | C₂H₅ | i-C₃H₇ | O | H | 4-Cl | H | |
| 54 | C₂H₅ | i-C₃H₇ | O | H | 4-Br | H | |
| 55 | C₂H₅ | i-C₃H₇ | O | H | 4-CN | H | |
| 56 | C₂H₅ | i-C₃H₇ | S | H | H | H | |
| 57 | C₂H₅ | i-C₃H₇ | S | H | 4-Cl | H | |
| 58 | C₂H₅ | i-C₃H₇ | S | H | 4-Br | H | |
| 59 | C₂H₅ | i-C₃H₇ | S | H | 4-CN | H | |
| 60 | C₂H₅ | i-C₃H₇ | O | H | 4-CN | H | |
| 61 | C₂H₅ | sec.-C₄H₉ | S | H | 4-Cl | H | |
| 62 | C₂H₅ | sec.-C₄H₉ | S | H | 4-Br | H | |
| 63 | C₂H₅ | sec.-C₄H₉ | S | H | 4-F | H | |
| 64 | C₂H₅ | sec.-C₄H₉ | S | H | 4-CN | H | |

-continued

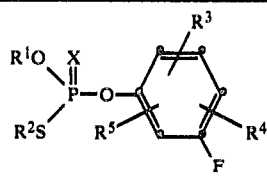

| No. | R$^1$ | R$^2$ | X | R$^3$ | R$^4$ | R$^5$ | $n_D$ |
|---|---|---|---|---|---|---|---|
| 65 | C$_2$H$_5$ | sec.-C$_4$H$_9$ | S | 6-Cl | 4-Cl | H | |
| 66 | C$_2$H$_5$ | i-C$_4$H$_9$ | O | H | H | H | $n_D^{24}$ = 1.4990 |
| 67 | C$_2$H$_5$ | i-C$_4$H$_9$ | O | H | 4-CN | H | |
| 68 | C$_2$H$_5$ | i-C$_4$H$_9$ | S | H | H | H | $n_D^{25}$ = 1.5307 |
| 69 | C$_2$H$_5$ | i-C$_4$H$_9$ | S | H | 4-Cl | H | |
| 70 | C$_2$H$_5$ | i-C$_4$H$_9$ | S | H | 4-Br | H | |
| 71 | C$_2$H$_5$ | i-C$_4$H$_9$ | S | H | 4-CN | H | |
| 72 | C$_2$H$_5$ | i-C$_4$H$_9$ | S | 6-Br | 4-Br | H | |
| 73 | C$_2$H$_5$ | i-C$_4$H$_9$ | S | H | 4-F | H | |
| 74 | C$_2$H$_5$ | i-C$_4$H$_9$ | S | H | 4-Cl | 6-Cl | |
| 75 | C$_2$H$_5$ | CH$_3$O(CH$_2$)$_2$— | O | H | 4-Cl | H | |
| 76 | C$_2$H$_5$ | C$_2$H$_5$O(CH$_2$)$_2$— | O | H | 4-Cl | H | |
| 77 | C$_2$H$_5$ | i-C$_3$H$_7$O(CH$_2$)$_2$— | O | H | H | H | |
| 78 | C$_2$H$_5$ | i-C$_3$H$_7$O(CH$_2$)$_2$— | O | H | 4-Cl | H | |
| 79 | C$_2$H$_5$ | i-C$_3$H$_7$O(CH$_2$)$_2$— | O | H | 4-Br | H | |
| 80 | C$_2$H$_5$ | i-C$_3$H$_7$O(CH$_2$)$_2$— | O | H | 4-CN | H | |
| 81 | C$_2$H$_5$ | i-C$_3$H$_7$O(CH$_2$)$_2$— | O | 6-Br | 4-Br | H | |
| 82 | C$_2$H$_5$ | i-C$_3$H$_7$O(CH$_2$)$_2$— | O | 6-Cl | 4-Cl | H | |
| 83 | C$_2$H$_5$ | C$_5$H$_9$ | O | H | H | H | |
| 84 | C$_2$H$_5$ | C$_5$H$_9$ | O | H | 4-Cl | H | |
| 85 | C$_2$H$_5$ | C$_5$H$_9$ | O | H | 4-Br | H | |
| 86 | C$_2$H$_5$ | C$_5$H$_9$ | S | H | H | H | |
| 87 | C$_2$H$_5$ | C$_5$H$_9$ | S | H | 4-Cl | H | |
| 88 | C$_2$H$_5$ | C$_5$H$_9$ | S | H | 4-Br | H | |
| 89 | C$_2$H$_5$ | CH$_3$—(CH$_2$)$_2$—CH(CH$_3$)— | O | H | H | H | |
| 90 | C$_2$H$_5$ | CH$_3$—(CH$_2$)$_2$—CH(CH$_3$)— | O | H | 4-Cl | H | |
| 91 | C$_2$H$_5$ | CH$_3$—(CH$_2$)$_2$—CH(CH$_3$)— | O | H | 4-Br | H | |
| 92 | C$_2$H$_5$ | ClCH$_2$—(CH$_2$)$_2$— | O | H | H | H | |
| 93 | C$_2$H$_5$ | ClCH$_2$—(CH$_2$)$_2$— | O | H | 4-Cl | H | |

The 3-fluorophenyl-(di)thiophosphoric acid esters of the formula I are suitable for effectively combating pests from the classes of insects, Acarina and nematodes. They may be used as pesticides for crop protection, and in the hygiene, stores protection and veterinary sector.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia keuhniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae,* and *Aporia crataegi*;

examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda*;

examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoseyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata*;

examples from the Hymenoptera order are *Athalia rosae, Hoplocampa minuta, Monomorium pharaonis, Solenopsis geminata,* and *Atta sexdens*;

examples from the Heteroptera order are *Nezara viridula, Eurygaster integriceps, Blissus leucopterus, Dysdercus cingulatus, Dysdercus intermedius, Piesma quadrata,* and *Lygus pratensis*;

examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes*

*persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;*

Examples from the Orthoptera order are *Forficula auricularia, Acheta domestica, Gryllotalpa gryllotalpa, tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, .e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dibius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, as formulations, or application forms prepared therefrom, e.g., as directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 4 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 13 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 19 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95% of active ingredient, or even the 100% active ingredient.

The amount of active ingredient applied in the open may vary from 0.2 to 10 kg/ha, and is preferably from 0.5 to 2.0 kg/ha.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethylphosphorodithioate, O-ethyl-S,S-dipropyl-phosphorodithioate, O,O-dimethyl-O-2,2-dichlorovinyl-phosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-bicarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropane carboxylate, (s)-alpha-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,-trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

The following examples demonstrate the biological action of the compounds. The prior art compounds O-ethyl-S-n-propyl-O-(2,4-dichlorophenyl)-thiolphosphate (German Printed Application DE-AS No. 2,163,391) and O-n-propyl-S-ethyl-O-(4-fluorophenyl)-thiolphosphate (Soviet Union Pat. No. 482,460) were used for comparison purposes.

The active ingredients according to the invention are numbered as in the foregoing table.

EXAMPLE 1

Contact action and effect of ingested food on caterpillars of the diamondback moth (*Plutella maculipennis*)

Leaves of young cabbage plants were dipped for 3 seconds in aqueous emulsions of the active ingredients, and, after briefly having allowed excess liquid to drip off, were placed on a moist filter paper in a Petri dish. 10 caterpillars of the 4th stage were then placed on the leaves. The action was assessed after 48 hours.

In this test, for example active ingredients nos. 1, 2, 3, 5, 6, 7, 8, 9, 10, 13, 14, 15, 17, 18, 19, 20, 22, 23, 24, 25, 29 and 32 had a better action than the prior art compounds.

EXAMPLE 2

Contact action on mosquito larvae (*Aedes aegypti*)

The active ingredient formulations were added to 200 ml of tapwater; 30 to 40 Aedes larvae in the 4th stage were then introduced.

The temperature was kept at 20° C. The action was assessed after 25 hours.

In this test, for example active ingredients nos. 4, 6, 10, 14, 17, 18, 20, 24, 25 and 29 had a better action than the prior art compounds.

EXAMPLE 3

Contact action on oriental cockroaches (*Blatta orientalis*)

The bottom of 1 liter preserving jars was lined with acetonic solutions of the active ingredients. After the solvent had evaporated, 5 adult cockroaches were introduced into each jar. The kill rate was determined after 48 hours.

In this test, active ingredients nos. 1, 2, 3, 4, 5, 6, 7, 8, 10, 13, 14, 15, 16, 19, 20, 21, 22, 23, 24, 25, 26, 27, 28, 29, 30, 31 and 32 had a better action than the prior art compounds.

EXAMPLE 4

Contact action on granary weevils (*Sitophilus granarius*)

Petri dishes 10 cm in diameter were lined with acetonic solutions of the active ingredients. After the solvent had evaporated, 100 granary weevils were placed in each dish.

After 4 hours, the weevils were transferred to untreated vessels. The kill rate was determined after 24 hours, by counting how many weevils were, after this period had elapsed, capable of leaving an untreated cardboard dish (40 mm in diameter, 10 mm high) within 60 minutes.

In this test, active ingredients nos. 2, 3, 5, 6, 7, 14, 15, 16, 19, 20, 21, 24, 25, 28, 29, 30 and 31 had a superior action.

EXAMPLE 5

Contact action on ticks (*Ornithodorus moubata*)

Ticks in the 3rd larval stage were placed in paper bags and dipped for 3 seconds in the candidate emulsions. The bags were then suspended. The action on the ticks was assessed after 48 hours.

In this test, active ingredients nos. 2, 5, 6, 7, 9, 14, 15, 16, 20, 21, 23, 25, 26, 31 and 32 had a good action.

EXAMPLE 6

Action on root-knot nematodes (*Meloidogyne incognita*)

Young tomato plants were planted in 500 g of compost heavily infested with root-knot nematodes. Treatment was carried out after 3 days by spraying, in a booth, 50 ml of aqueous formulations of the active ingredients.

The roots were checked for root-knots after 6 to 8 weeks.

In this test, for example active ingredients nos. 1, 2, 3, 4, 5, 6, 7, 8, 11, 14, 20, 21 and 29 had a superior action.

EXAMPLE 7

Action on spider mites (*Tetranychus telarius*)

Potted bush beans which had developed the first pair of true leaves and were under heavy attack from spider mites (*Tetranychus telarius*) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

In this test, for example active ingredients nos. 3, 13 and 17 had a superior action.

EXAMPLE 8

Continuous contact action on houseflies (*Musca domestica*)

Both covers and bottoms of Petri dishes 10 cm in diameter were lined with a total per dish of 2 ml of acetonic solutions of the active ingredients. After the solvent had evaporated (about 30 mins.), 20 4-day old flies were introduced into each dish.

The kill rate was determined after 4 hours.

In this test, a very high kill rate was achieved with active ingredients nos. 1 to 32.

EXAMPLE 9

Contact action on cotton stainers (*Dysdercus intermedius*)

Petri dishes 10 cm in diameter were lined with 1 ml of acetonic solutions of the active ingredients. After the solvent had evaporated, 20 larvae of the penultimate stage were placed in the dishes, and the effect was registered after 24 hours.

In this test, active ingredients nos. 2, 3, 5, 6, 9, 19, 20, 21, 23, 31 and 32 had a superior action.

Contact action on cockroaches (*Blatta orientalis*)

The bottoms of 1 liter preserving jars was treated with acetonic solutions of the active ingredients.

After the solvent had evaporated, 5 adult cockroaches were placed in each jar.

The kill rate was determined after 48 hours.

| Sample no. | [mg] | [% mortality] |
|---|---|---|
| 1 | 0.1 | 100 |
| 2 | 0.05 | 100 |
| 3 | 0.05 | 100 |
| 4 | 0.1 | 100 |
| 5 | 0.05 | 100 |
| 6 | 0.05 | 100 |
| 7 | 0.05 | 80 |
| 8 | 0.05 | 80 |
| 10 | 0.1 | 100 |

-continued

| Sample no. | [mg] | [% mortality] |
|---|---|---|
| 13 | 0.05 | 80 |
| 14 | 0.1 | 100 |
| 15 | 0.1 | 100 |
| 16 | 0.1 | 100 |
| 19 | 0.05 | 100 |
| 20 | 0.05 | 100 |
| 21 | 0.1 | 100 |
| 22 | 0.05 | 80 |
| 23 | 0.1 | 100 |
| 24 | 0.02 | 80 |
| 25 | 0.05 | 100 |
| 26 | 0.05 | 100 |
| 27 | 0.1 | 100 |
| 28 | 0.05 | 100 |
| 29 | 0.05 | 100 |
| 30 | 0.02 | 100 |
| 31 | 0.05 | 100 |
| 32 | 0.02 | 80 |
| Comparative agent II | 1.0 | 50 |

Continuous contact action on houseflies (*Musca domestica*)

The insides of Petri dishes 10 cm in diameter were treated with acetonic solutions of the active ingredients.

After evaporation of the solvent, 20 4-day old houseflies were placed in each dish.

The kill rate was determined after 4 hours.

| Sample no. | [mg] | [% mortality] |
|---|---|---|
| 1 | 0.005 | 100 |
| 2 | 0.005 | 100 |
| 3 | 0.01 | 100 |
| 4 | 0.005 | 100 |
| 5 | 0.02 | 100 |
| 6 | 0.005 | 100 |
| 7 | 0.01 | 100 |
| 8 | 0.02 | 100 |
| 9 | 0.02 | 100 |
| 10 | 0.01 | 100 |
| 11 | 0.02 | 100 |
| 12 | 0.01 | 100 |
| 13 | 0.02 | 100 |
| 14 | 0.02 | 100 |
| 15 | 0.02 | 100 |
| 19 | 0.002 | 80 |
| 20 | 0.005 | 80 |
| 21 | 0.005 | 100 |
| 22 | 0.02 | 100 |
| 23 | 0.01 | 100 |
| 24 | 0.005 | 100 |
| 25 | 0.01 | 100 |
| 27 | 0.02 | 100 |
| 28 | 0.02 | 100 |
| 29 | 0.02 | 100 |
| 30 | 0.002 | 80 |
| 31 | 0.005 | 80 |
| 32 | 0.005 | 80 |

Contact action on mosquito larvae (*Aedes aegypti*)

Formulations of the active ingredients were added to 200 ml of tapwater; 30 to 40 mosquito larvae in the 4th larval stage were then introduced.

The temperature was kept at 20° C. The action was determined after 24 hours.

| Sample no. | [ppm] | [% mortality] |
|---|---|---|
| 4 | 0.01 | 100 |
| 6 | 0.02 | 100 |
| 10 | 0.02 | 100 |
| 14 | 0.01 | 100 |

-continued

| Sample no. | [ppm] | [% mortality] |
|---|---|---|
| 17 | 0.04 | 100 |
| 18 | 0.02 | 100 |
| 20 | 0.02 | 100 |
| 24 | 0.02 | approx. 80 |
| 25 | 0.02 | 100 |
| 29 | 0.02 | 100 |
| Comparative agent I | 0.08 | 100 |

Contact action on granary weevils (*Sitophilus granarius*)

Petri dishes of 10 cm in diameter were lined with acetonic solutions of the active ingredients. After the solvent had evaporated, 100 granary weevils were placed in each dish.

After 4 hours, the weevils were transferred to untreated vessels. The kill rate was determined after 24 hours, by counting how many weevils were, after this period had elapsed, capable of leaving an untreated cardboard dish (40 mm in diameter, 10 mm high) within 60 minutes.

| Sample no. | [mg] | [% mortality] |
|---|---|---|
| 2 | 0.02 | 100 |
| 3 | 0.02 | 100 |
| 5 | 0.01 | 80 |
| 6 | 0.01 | 80 |
| 7 | 0.01 | 80 |
| 14 | 0.01 | 80 |
| 15 | 0.02 | 100 |
| 16 | 0.02 | 100 |
| 19 | 0.02 | 100 |
| 20 | 0.02 | 100 |
| 21 | 0.01 | 80 |
| 24 | 0.01 | 80 |
| 25 | 0.01 | 80 |
| 28 | 0.01 | 80 |
| 29 | 0.02 | 100 |
| 30 | 0.02 | 100 |
| 31 | 0.01 | 100 |
| Comparative agent I | 0.02 | 80 |

Contact action and effect of ingested food on caterpillars of the diamondback moth (*Plutella maculipennis*)

Leaves of young cabbage plants were dipped for 3 seconds in aqueous emulsions of the active ingredients, and placed, after excess liquid had been briefly allowed to drip off, on a moist filter paper in a Petri dish. 10 caterpillars in the 4th stage were then placed on each leaf.

The action was assessed after 48 hours.

| Sample no. | [%] | [% mortality] |
|---|---|---|
| 1 | 0.001 | approx. 80 |
| 2 | 0.002 | 100 |
| 3 | 0.002 | 100 |
| 5 | 0.0004 | 100 |
| 6 | 0.002 | 100 |
| 7 | 0.002 | 100 |
| 9 | 0.001 | 100 |
| 10 | 0.002 | approx. 80 |
| 13 | 0.0004 | 100 |
| 14 | 0.0004 | 100 |
| 15 | 0.002 | 100 |
| 17 | 0.0004 | approx. 80 |
| 18 | 0.0004 | approx. 80 |
| 19 | 0.001 | approx. 80 |
| 20 | 0.001 | approx. 80 |
| 22 | 0.002 | 100 |

-continued

| Sample no. | [%] | [% mortality] |
|---|---|---|
| 23 | 0.001 | approx. 80 |
| 24 | 0.001 | approx. 80 |
| 25 | 0.001 | 100 |
| 29 | 0.001 | approx. 80 |
| 32 | 0.005 | approx. 80 |
| Comparative agent II | 0.1 | 50 |

Contact action on cotton stainers (*Dysdercus intermedius*)

Petri dishes 10 cm in diameter were lined with 1 ml of acetonic solutions of the active ingredients.

After the solvent had evaporated, 20 larvae in the penultimate stage were placed in each dish and the action was registered after 24 hours.

| Sample no. | [mg] | [% mortality] |
|---|---|---|
| 2 | 0.002 | 100 |
| 3 | 0.002 | 100 |
| 5 | 0.005 | 100 |
| 6 | 0.005 | 100 |
| 9 | 0.005 | 100 |
| 19 | 0.005 | 100 |
| 20 | 0.005 | 100 |
| 21 | 0.005 | 100 |
| 23 | 0.005 | 100 |
| 31 | 0.005 | 100 |
| 32 | 0.005 | 100 |
| Comparative agent I | 0.005 | 80 |

Action on spider mites (*Tetranychus telarius*)

Potted bushbeans which had developed the first pair of true leaves and were under heavy attack from all stages of spider mites (*Tetranychus telarius*) were sprayed to runoff from all sides in a spray cabinet with 50 ml of aqueous formulations of the active ingredients. Spraying lasted for about 22 seconds.

The plants were investigated after 8 days for signs of living mites.

| Sample no. | [mg] | [% mortality] |
|---|---|---|
| 3 | 0.01 | 100 |
| 13 | 0.01 | approx. 90 |
| 17 | 0.01 | approx. 90 |
| Comparative agent I | 0.02 | 100 |
| Comparative agent II | 0.1 | <50 |

Contact action on ticks (*Ornithodorus moubata*)

Ticks on the 2nd larval stage were placed in teabags and dipped for 3 seconds in the candidate emulsion. The bags were then suspended. The action on the ticks was assessed after 48 hours.

| Sample no. | [mg] | [% mortality] |
|---|---|---|
| 2 | 0.001 | 80 |
| 5 | 0.002 | 100 |
| 6 | 0.002 | 100 |
| 7 | 0.0004 | 100 |
| 9 | 0.002 | 100 |

-continued

| Sample no. | [mg] | [% mortality] |
|---|---|---|
| 14 | 0.001 | 100 |
| 15 | 0.001 | 100 |
| 16 | 0.002 | 100 |
| 20 | 0.001 | 80 |
| 21 | 0.002 | 100 |
| 23 | 0.001 | 100 |
| 25 | 0.001 | 100 |
| 26 | 0.001 | 100 |
| 31 | 0.002 | 100 |
| 32 | 0.002 | 100 |

Action on root-knot nematodes (*Meloidogyne incognita*)

Garden soil heavily infested with *Meloidogyne incognita* was split into 300 g portions which were intimately mixed with 30 ml of 0.1% aqueous active ingredient formulations and filled into flower pots. Tomato plants were then placed in the soil prepared in this manner, and the pots were kept under greenhouse conditions at 25° to 26° C.

After 6 to 8 weeks root attack was assessed.

| Sample no. | [ppm] | [root-knot formation] |
|---|---|---|
| 1 | 100 | none |
| 2 | 100 | none |
| 3 | 100 | none |
| 4 | 100 | none |
| 5 | 100 | none |
| 6 | 100 | none |
| 7 | 100 | none |
| 8 | 100 | none |
| 11 | 100 | none |
| 14 | 100 | none |
| 20 | 100 | none |
| 21 | 100 | none |
| 29 | 100 | none |
| Comparative agent II | 100 | extensive |

We claim:

1. A 3-fluorophenyl(di)thiophosphate of the formula

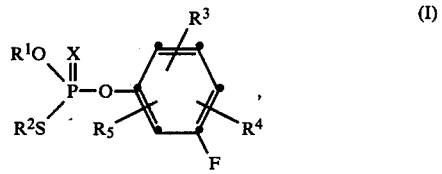

where $R^1$ is alkyl of 1 to 3 carbon atoms, $R^2$ is alkyl or haloalkyl of 1 to 5 carbon atoms or alkoxyalkyl of 2 to 8 carbon atoms, $R^3$, $R^4$ and $R^5$ independently of one another are each hydrogen, chlorine or bromine and X is oxygen or sulfur.

2. A compound of the formula I as set forth in claim 1, wherein $R^2$ is alkyl of 3 to 4 carbon atoms, chloroalkyl of 3 to 4 carbon atoms, or alkoxyalkyl of 3 to 5 carbon atoms.

3. A compound of the formula I as set forth in claim 1, wherein $R^2$ is an alkyl of 3 to 4 carbon atoms.

4. A process for combating pests, wherein a 3-fluorophenyl(di)thiophosphate of the formula I as set forth in claim 1 is allowed to act on the pests or their habitat.

5. A pesticide containing a solid or liquid carrier and an effective amount of a 3-fluorophenyl(di)thiophosphate of the formula I as set forth in claim 1.

* * * * *